United States Patent
Daneluzzi

(10) Patent No.: US 10,029,087 B2
(45) Date of Patent: Jul. 24, 2018

(54) DISINFECTION DEVICE FOR CONNECTORS

(71) Applicant: NEX MEDICAL S.R.L., Casorezzo (MI) (IT)

(72) Inventor: Silvio Daneluzzi, Cerro Maggiore (IT)

(73) Assignee: NEX MEDICAL ANTISEPTICS S.R.L., Casorezzo (IT)

( * ) Notice: Subject to any disclaimer, the term of this patent is extended or adjusted under 35 U.S.C. 154(b) by 5 days.

(21) Appl. No.: 15/024,669

(22) PCT Filed: Sep. 26, 2014

(86) PCT No.: PCT/IB2014/064860
§ 371 (c)(1),
(2) Date: Mar. 24, 2016

(87) PCT Pub. No.: WO2015/044904
PCT Pub. Date: Apr. 2, 2015

(65) Prior Publication Data
US 2016/0213912 A1    Jul. 28, 2016

(30) Foreign Application Priority Data

Sep. 30, 2013  (IT) .............................. MI2013A1610

(51) Int. Cl.
| | |
|---|---|
| A61M 39/16 | (2006.01) |
| A61L 2/18 | (2006.01) |
| A61M 39/20 | (2006.01) |
| A61L 2/235 | (2006.01) |
| A61B 1/12 | (2006.01) |

(52) U.S. Cl.
CPC ............. *A61M 39/165* (2013.01); *A61L 2/18* (2013.01); *A61L 2/235* (2013.01); *A61M 39/20* (2013.01); *A61B 1/122* (2013.01); *A61L 2202/24* (2013.01); *A61M 2209/10* (2013.01)

(58) Field of Classification Search
CPC ........................... A61M 39/165; A61M 39/162
USPC .......................................................... 422/292
See application file for complete search history.

(56) References Cited

U.S. PATENT DOCUMENTS

| | | | | |
|---|---|---|---|---|
| 4,203,857 A | * | 5/1980 | Dugan | ..................... A47K 7/03 15/104.93 |
| 2010/0003067 A1 | * | 1/2010 | Shaw | .................... A61M 39/16 401/206 |
| 2010/0106103 A1 | * | 4/2010 | Ziebol | ..................... A61L 2/186 604/265 |
| 2010/0172794 A1 | | 7/2010 | Ferlic et al. | |
| 2010/0200017 A1 | | 8/2010 | Kerr et al. | |

(Continued)

OTHER PUBLICATIONS

Lide et al, CRC Handbook of Chemistry and Physics, Internet Version 2005, <http://www.hbcpnetbase.com>, CRC Press, Section 15-29.*

*Primary Examiner* — Kevin Joyner
*Assistant Examiner* — Holly M Mull
(74) *Attorney, Agent, or Firm* — Pearne & Gordon LLP

(57) ABSTRACT

A device for disinfecting catheter connectors comprising a container (2) having a closed lower base end (2b) and an opposite open upper end (2a) and a sponge-like element (3) inserted inside the container (2), impregnated with a liquid medical substance (4). The sponge-like element (3) has an axial through cavity (5) within it and a semi-rigid insert (6) housed in the cavity (5).

18 Claims, 3 Drawing Sheets

(56) References Cited

U.S. PATENT DOCUMENTS

| | | | |
|---|---|---|---|
| 2011/0030726 A1* | 2/2011 | Vaillancourt | A61B 1/122 |
| | | | 134/6 |
| 2011/0064512 A1 | 3/2011 | Shaw et al. | |
| 2011/0184382 A1* | 7/2011 | Cady | A61L 2/26 |
| | | | 604/506 |
| 2012/0302997 A1 | 11/2012 | Gardner et al. | |
| 2012/0315201 A1 | 12/2012 | Ferlic et al. | |
| 2015/0117932 A1* | 4/2015 | Russell | A61L 2/18 |
| | | | 401/196 |

\* cited by examiner

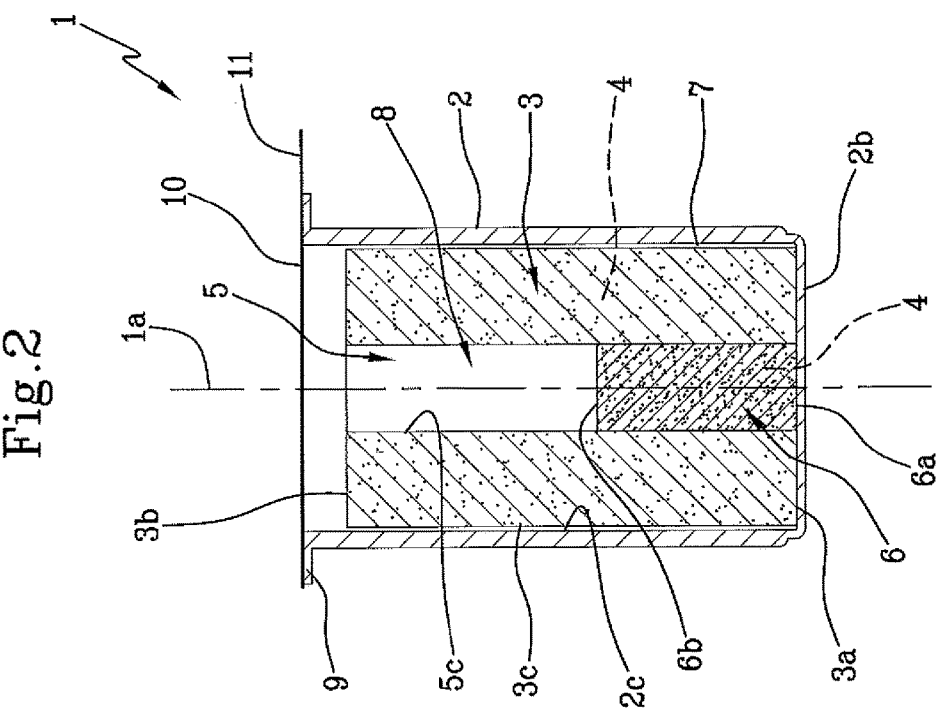
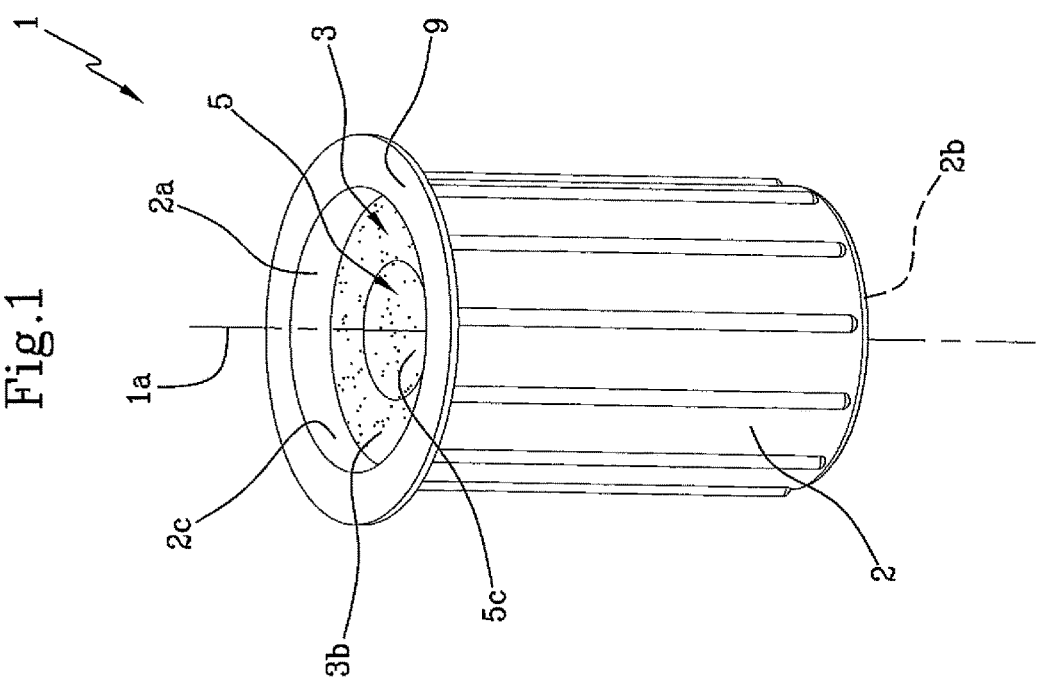

DISINFECTION DEVICE FOR CONNECTORS

The present invention relates to a device for disinfecting catheter connectors.

Catheter connectors are medical devices connectable to peripheral vein access devices used to administer medications intravenously. They provide a point of access without representing, however, an entry for microbial contaminants. Catheters are of vital importance for patients and thus ensuring the asepsis of the connectors is fundamental.

In particular, the needleless connector represents one of the most advanced access systems available in the market.

The needleless connector for infusions is a closed valve system consisting of a hermetic silicone or rubber closure, to which a needleless syringe or infusion set can be directly connected to permit the passage of liquids through the connector. The mechanism is built to ensure that, when the route is open, there is no contact between the outer surfaces of the connector closure and the injected liquid.

In particular, before making any connection, in order to avoid possible risks of infection, new international guidelines in this sector recommend not only carrying out a procedure to disinfect the connector by swabbing the end and thread, but also thoroughly scrubbing the front with a chlorhexidine-based alcoholic solution.

The valve system must be directly connected to the vascular catheter; consequently, every manoeuvre tied to it requires observance of aseptic techniques.

The use of needleless connectors for infusions is aimed at avoiding the use of needles and the consequent risk of accidental punctures, as well as at providing a better barrier against bacterial contaminations through the intraluminal route, greater protection of the catheter and greater simplicity in the manoeuvres of managing the infusion line. However, the needleless connector does not in itself reduce the risk of infection: it is necessary, therefore, to rigorously apply the methods of disinfecting the connector prior to every access and the "no touch" technique, as well as, naturally, correctly washing one's hands.

In particular, before making any connection, in order to avoid possible risks of infection, new international guidelines in this sector recommend not only carrying out a procedure to disinfect the connector by swabbing the end and thread, but also thoroughly scrubbing the front with a chlorhexidine-based alcoholic solution. The devices currently present on the market comprise a disinfection cap designed for the purpose of disinfecting the upper part and thread of luer lock needleless connectors for intravenous infusions with 70% isopropyl alcohol while they are connected to the hub.

The cap consists of a receptacle having an edge at the open end provided with an internal thread such as to be screwed onto the free end of the connector.

Contained inside the receptacle there is a small pad impregnated with a disinfectant substance. The open end of the receptacle is closed off by a protective film which is removable at the time of use of the cap.

When screwed onto the thread of the connector of the line access devices and left thereupon for the whole time the connector is not used, the disinfection cap protects the latter from atmospheric contamination and direct contact. The main problem of this device is that it does not ensure a perfect sterility of the covered part over time. The alcoholic solution contained in a small pad inside it can become contaminated over time and is not sufficient to ensure the perfect sterility of the outer part of the connector. Moreover, since its use is prolonged over time, there is no guarantee that the disinfectant solution will last for the whole duration. The particular configuration of the device precludes being able to apply the right amount of disinfectant solution on the connector so that only a small dose of disinfectant solution is released, usually a small fraction of a milliliter.

Furthermore, the disinfection cap does not enable a perfect mechanical cleaning action on the whole surface of the connector.

Moreover, the distribution of the disinfectant liquid over the connector is not controllable by the operator and hence the possible risk of a resulting contamination suggests reapplying the disinfectant solution on the connector once the cap has been removed, thus losing in part the benefits of using it.

It has also been found that due to the fact that the cap is screwed onto the connector, the stroke of the latter inside the cap is limited by the extent of the thread, which also precludes any possibility of moving the cap around the connector and exerting a mechanical action, which would contribute to a better cleaning of the connector.

A further product present on the market consists in moistened disposable wipes. These wipes are used to disinfect the connectors prior to use. Their main disadvantage is represented by impossibility of using the no-touch technique, since the operator must grasp the wipes to use them.

Moreover, the shape and materials used for the wipes do not allow an effective mechanical action on the front part of the connector. The manipulation of the wipe during the disinfection operation very often provokes tearing of the wipe material, thus precluding a complete disinfection of the surface of the connector and leaving dangerous fibre residues on the connector.

In this context, the technical task at the basis of the present invention is to propose a device for disinfecting catheter connectors that overcomes the aforementioned drawbacks of the prior art.

In particular, it is an object of the present invention to provide a device for disinfecting catheter connectors that assures the perfect asepticity of the connector, avoiding any type of risk of infection.

Furthermore, an object of the present invention is produce a device for catheter connectors that is easy to use, is disposable and assures excellent cleaning of every exposed surface of the catheter connector, also with an effective mechanical action, avoiding any contact between the user's hands and the connector itself.

The stated technical task and specified object are substantially achieved by a device for disinfecting catheter connectors comprising the technical features disclosed in one or more of the appended claims.

Additional features and advantages of the present invention will become more apparent from the approximate, and thus non-limiting, description of a preferred, but non-exclusive embodiment of a device for disinfecting catheter connectors, as illustrated in the appended drawings in which:

FIG. 1 is a perspective view of a device for disinfecting catheter connectors according to the present invention;

FIG. 2 is a sectional view of the device for disinfecting catheter connectors of FIG. 1, in a closed configuration of non-usage;

Figure 3:
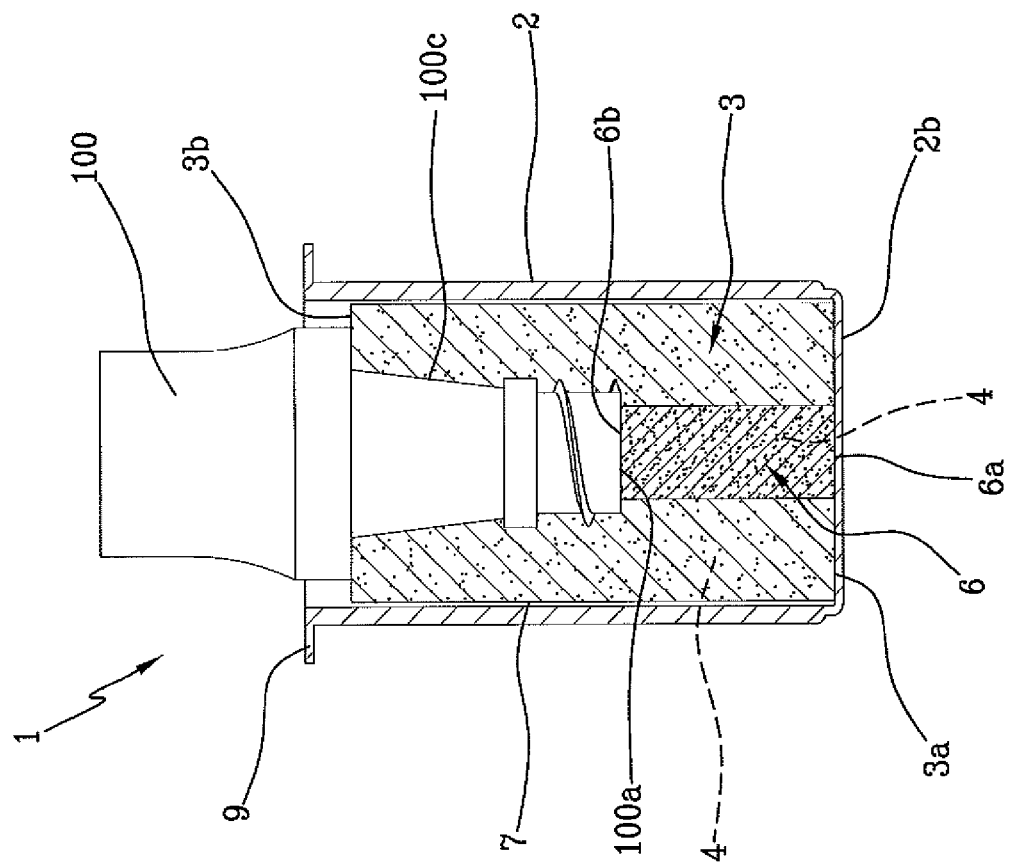
FIG. 3 is a sectional view of the device for disinfecting catheter connectors in an open operational condition during use with a catheter connector.
Figure 4:
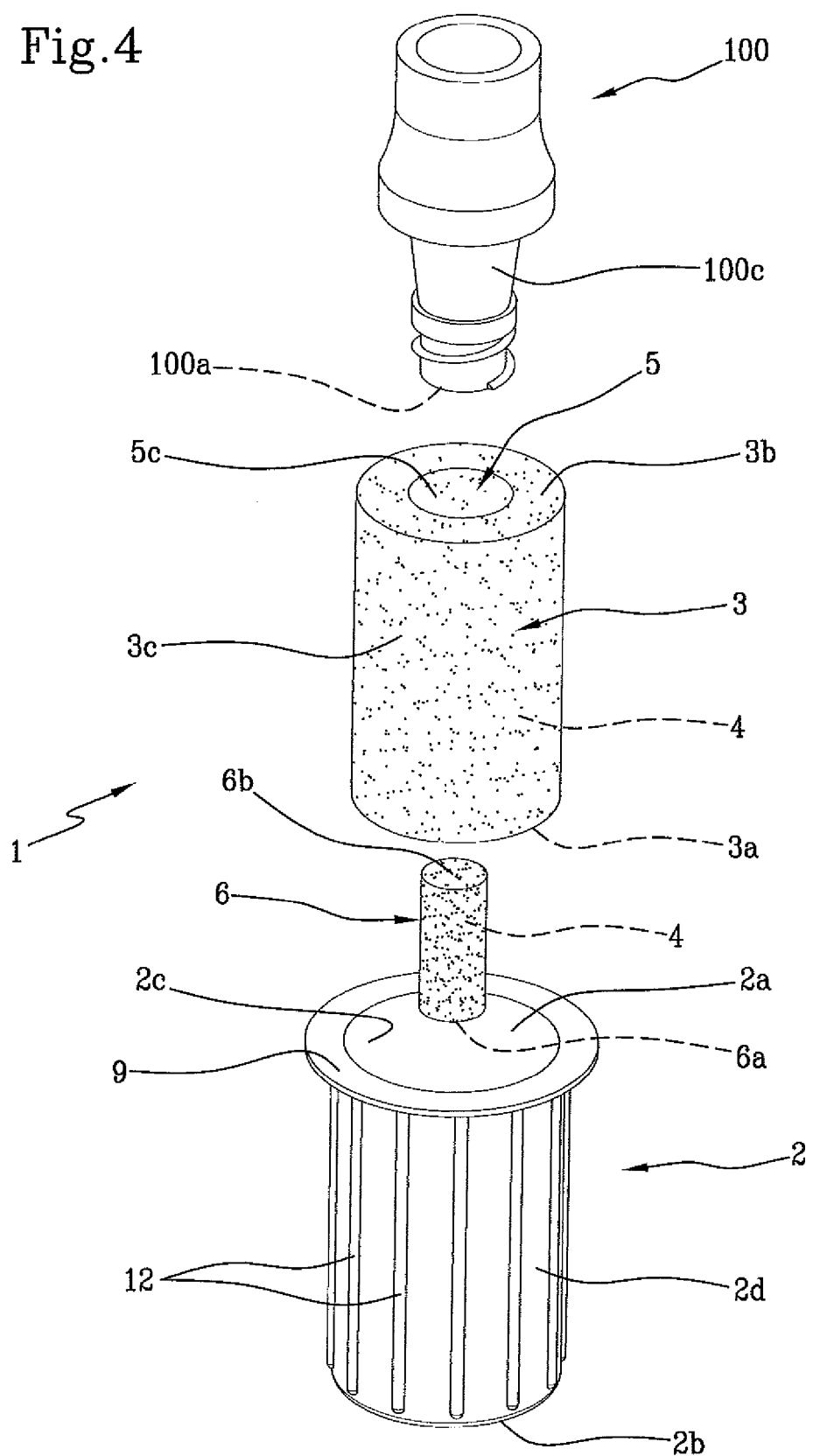
FIG. 4 is an exploded view of the device for disinfecting catheter connectors according to the present invention.

With reference to the appended figures, 1 denotes overall a device for disinfecting connectors 100 of catheters in accordance with the present invention.

The device 1 comprises an outer container 2, preferably cylindrical in the shape of a beaker, hollow on the inside and having a closed lower base end 2b and an opposite open upper end 2a.

Inserted inside the outer container 2 there is a sponge-like element 3, impregnated with a liquid medical substance 4.

This substance 4 can be, for example, an alcoholic chlorhexidine disinfectant solution.

The sponge-like element 3 advantageously has the same internal shape as the container 2; therefore, it is preferably cylindrical in shape, with an outside diameter only slightly smaller than the inside diameter of the container 2; thus, between the internal lateral wall 2c of the container 2 and the external lateral surface 3c of the sponge-like element 3 there is an air gap 7 that enables the latter to undergo a lateral expansion when in use, as will be explained below.

A first end 3a of the sponge-like element goes to rest against the closed base end 2b of the container 2, whilst a second end 3b is turned toward the outside of the container 2.

The sponge-like element 3 has a central axial through cavity 5, which is longitudinal and coaxial with the axis 1a of the outer container 2 and extends between the two ends 3a and 3b.

The cavity 5 advantageously has a diameter preferably comprised between 2 and 8 mm, even more preferably between 3 and 6 mm, and a length preferably comprised between 20 and 35 mm, even more preferably between 25 and 30 mm.

The cavity 5 is adapted to house a generic catheter connector 100, which is inserted inside it so as to be disinfected thanks to the mechanical rubbing action exerted by the sponge-like element 3 (which is made to rotate about its axis 1a and slide axially along it) and the contact with the disinfectant liquid, with which the sponge-like element 3 is impregnated and which is released onto the connector as a result of a slight compression that the sponge-like element 3 undergoes.

The diameter of the internal cavity 5 of the sponge-like element 3 is normally smaller than the outside diameter of a generic connector 100 insertable into the cavity 5 to be disinfected. The size of the inside diameter of the cavity 5, smaller than the outside diameter of the connector, allows a perfect adhesion of the internal surface 5c of the cavity 5 to the external surface 100c of the connector to be disinfected, enabling complete contact and a better action of mechanical rubbing of the sponge-like element 3 on the lateral walls of the connector, as well as the release of the antiseptic over the whole surface of the connector.

In fact, given the reduced size of the cavity 5 compared to the overall transverse dimensions of the connector 100, the sponge-like element 3 tends to expand, slightly compressing its lateral walls and thus facilitating the discharge of the disinfectant liquid 4. The air gap 7 between the external lateral walls 3c of the sponge-like element 3 and the internal lateral wall 2c of the container 2 permits a correct expansion of the sponge-like element 3 following the insertion of the connector 100, so that the right amount of disinfectant liquid is released. In the absence of the gap, the sponge-like element 3 would be completely compressed between the connector 100 and the container 2, with the risk of releasing an excessive amount of liquid.

Inside the cavity 5 of the sponge-like element 3 there is a semi-rigid insert 6, advantageously fitted to measure. The latter advantageously has a cylindrical shape, with a diameter coinciding or in any case not smaller than the diameter of the internal cavity 5 of the sponge-like element 3, whereas it extends axially or is of a lower height than the sponge-like element 3. Advantageously, the insert 6 extends axially or is of a height, along the axis 1a of the device, comprised between one fifth and one half of the height of the sponge-like element 3.

The cylindrical insert 6 inside the cavity 5 has a lower base end 6a aligned with the first end 3a of the sponge-like element 3. Therefore, the first end 3a of the sponge-like element 3 and the lower base end 6a of the semi-rigid insert 6 are coplanar and advantageously constrained, glued or heat-sealed, to the internal base 2b of the container 2. In this manner, they are solidly joined with the container 2 itself during the manipulation of the device (rotations and rubbing around the connector), which enables the sponge-like element 3 and the insert 6 to rotate integrally with the housing or container 2, thereby enabling a better and more effective scrubbing of the front and lateral surfaces of the connector by the insert and the lateral walls of the sponge-like element.

The positioning of the semi-rigid cylindrical insert 6 in the lower end of the cavity 5 creates a blind cavity 8 inside the sponge-like element 3. The blind cavity 8 is thus laterally delimited by the internal walls 5c of the cavity 5 of the sponge-like element 3 and at the bottom by the surface of the upper end 6b of the insert 6, opposite the lower base end 6a constrained to the container 2.

This particular cavity 8 is of an ideal conformation for the insertion and disinfection of the connector 100, which, once inserted, is completely enveloped by the porous material of the sponge-like element 3 and of the semi-rigid insert 6 which releases the disinfectant substance 4.

The surface of the upper end 6b of the insert 6, which forms the base of the blind cavity 8, can be flat, undulated or rough.

The particular design of the cylindrical insert 6 placed at the lower end of the cylindrical cavity 5 of the sponge-like element 3 moreover permits, through the rotational movement of the device 1 around its axis 1a, an effective scrubbing of the front part 100a of the connector, one of the most critical areas for the possible risks of infection.

The height dimensioning of the sponge-like element 3 and of the insert 6 makes it possible to obtain a length of the internal blind cavity 8 that is sufficient to completely accommodate the length of the connector 100.

The material of the sponge-like element 3 consists of a soft, absorbent, porous low- or medium density material, such as, for example, compact polyolefin fibres (PE, PP, PET), which permit the absorption of the disinfectant and the release thereof upon contact with the connector.

Preferably, sponges, polyurethane or foams are not used for the sponge-like element 3.

The fibres also act mechanically (scrubbing action) on the surfaces of the connector.

The sponge-like element 3 is made of a soft, absorbent, porous low- or medium density material, with a density comprised between 0.05 and 0.15 g/cc, preferably 0.108 g/cc.

The material of the insert 6 has a higher density than the material making up the sponge-like element 3, comprised between 0.1 g/cc and 0.5 g/cc, preferably 0.38 g/cc.

The insert 6 has a compact circular surface that is denser in order to enable better scrubbing and friction on the front part 100a of the connector.

The sponge-like element 3 and the small insert 6 are impregnated with about 3-4 ml of disinfectant solution. The disinfectant solution is thus dispersed over the connector during the rubbing over the external surfaces.

The insert 6 can be made of absorbent or non-absorbent material, for example rubber. Rubbing the connector on the internal lateral walls of the sponge-like element 3 favours the flow of fluid on the upper surface of the insert, enabling both a scrubbing and disinfection of the front surface of the connector.

The outer container 2 preferably has a cylindrical shape with a circular cross section, but cross sections having different shapes such as, for example, square or rectangular, are not excluded.

The container 2 enables the sponge-like element 3 to be correctly housed inside it.

The particular configuration of the container 2 together with the described dimensioning of the sponge-like element 3 make it possible to house and disinfect any connector present on the market, irrespective of the particular shape adopted by the manufacturer.

As said previously, the container 2 has an inside diameter that is larger than the diameter of the sponge-like element 3, in order to permit a slight lateral expansion thereof following the insertion of the connector 100 in the blind cavity 8, the latter being normally of a smaller diameter than the connector. In particular, the cylinder-shaped container 2 acts like primary packaging for the sponge-like element 3. It perfectly encloses the sponge-like element 3, protecting it from atmospheric contamination and direct contact with the operator's hands, thus permitting the no-touch technique during the operations of disinfecting the connector.

The outer cylinder-shaped container 2 is made of a plastic material such as PE or PP or in any case a thermoformed or injection-moulded plastic material.

The outer container 2 has a flanged annular edge 9 at the upper end 2a thereof.

The outer container 2 is sealed by means of a foil 10 of aluminium or plastic material heat-sealed onto the annular edge 9.

The protective foil 10 has a side pull tab 11 which permits easy opening of the foil itself.

The outer container 2 advantageously has vertical longitudinal ridges 12 on its external lateral surface 2d. These ridges 12 serve as an external grip for improving the hold on the device during the use thereof.

The material of the container is made in such a way as to be flexible. This feature enables the operator to exert slight pressure on the outside of the device during the operation of disinfecting the connector; this provokes pressure on the sponge-like element 3, favouring the discharge of the disinfectant liquid through the pores of the sponge-like element 3 and the correct distribution of the antiseptic solution on the surface of the connector 100 and increasing the action of friction and disinfection on the connector itself.

In this regard, a variant of the primary packaging of the sponge-like element 3 envisages a soft or semi-rigid heat-sealable film applicable to the external wall of the sponge-like element 3 as well as to the external base of the first end 3a. In this manner it is even more functional and easier to press on the outside of the device with one's fingers, so as to press on the sponge-like element 3 from the outside and cause the liquid to flow over the connector. This permits a better possibility for the operator to adapt the pressure of the sponge-like element on the connector and thus also the rubbing friction.

There can also be envisaged the possibility of an automatic operation by inserting the disinfecting device in a portable electrical unit (battery operated, for example) which ensures the scrubbing time required by regulatory guidelines and a larger number of rotation cycles per unit of time.

The particular form of the sponge-like element 3, which acts as a pad, enables the connector to be accommodated, enveloped and enclosed completely, ensuring a perfect disinfection of all external parts of the connector.

After the connector has been inserted into the blind cavity 8 of the sponge-like element 3, the disinfection operation consists in rotating the device 1 with semi-rotations in both directions about the axis 1a, so as to thoroughly scrub and disinfect all around the thread of the connector in complete asepsis, that is, without it coming directly into contact with the operator's hands.

The operator can manipulate the device simply by holding the outer container 2 between his or her fingers, avoiding any interference with and/or contamination of the internal part of the device.

The device thus conceived is disposable, since after the protective foil 10 has been removed it is used immediately and disposed of at the end of the disinfection. The device is employed just prior to use of the needleless connector for intravenous infusions, taking samples, etc, so as to perfectly disinfect the front and upper parts and thread of the connector and not remain connected to the latter passively for a lengthy time, as is the case with prior art devices: in fact, throughout the time of contact, in general thirty seconds, the device is constantly manipulated around the connector. Thanks to its particular configuration, once used and before being disposed of, the device can be utilized to remove organic residues present on the connector as a result of the operations of inserting and detaching the connector itself.

The particular configuration of the device, thanks to the semicircular rotations applied by the operator and the type of material used for the two internal pads, ensures effective mechanical friction between the internal walls of the cavity and the threaded and front surfaces of the connector.

Moreover, thanks to the particular configuration and low porosity of the insert, the antiseptic is all conveyed—by pressing ones fingers on the sponge-like element—onto the upper surface of the insert itself, ensuring maximum effectiveness in disinfecting the front surface of the connector and without dispersals or imbibitions that would decrease the effectiveness of the disinfecting device.

The invention claimed is:

1. A device for disinfecting a catheter connector, comprising a container (2) having a closed lower base end (2b) and an opposite open upper end (2a), a sponge-like element (3) inserted inside said container (2) and being impregnated with a liquid medical substance (4) and adapted to exert a rubbing action on an outer lateral surface of a catheter connector, said sponge-like element (3) having an axial through cavity (5) within it; the through cavity (5) having a lateral surface, the device further comprising a semi-rigid insert (6) having a top, a bottom and an outer lateral surface and being housed in said cavity (5), the outer lateral surface of the semi-rigid insert (6) which is adjacent the top of the semi-rigid insert (6) engaging the adjacent lateral surface of the through cavity (5), the semi-rigid insert (6) being sized and adapted so that it exerts a rubbing action only on a base outer surface of said catheter connector, wherein said semi-rigid insert (6) has a density greater than the density of said sponge-like element (3), the portion of the bottom of the sponge-like element (3) which is adjacent the bottom of the through cavity (5) being coplanar with the bottom of the semi-rigid insert (6), the insert (6) having a longitudinal extent along an axis (1a) of the container (2) that is shorter than that of the sponge-like element (3).

2. The device according to claim 1, characterized in that said insert (6) is bottomed on the bottom of said cavity (5), in contact with the base end (2b) of the container (2), so as to form a blind cavity (8) that is open toward the open upper end (2a) of the container (2).

3. The device according to claim 2, characterized in that said cavity (5) has a diameter that is smaller than an outside diameter of a catheter connector (100) insertable inside it.

4. The device according to claim 1, characterized in that said sponge-like element (3) and said insert (6) are constrained to the lower base end (2b) of said container (2).

5. The device according to claim 1, characterized in that an upper end (6b) of the insert (6) has a flat, undulated or rough surface.

6. The device according to claim 1, characterized in that said sponge-like element (3) is made from a soft, absorbent, porous low- or medium density material, comprised between 0.05 and 0.15 g/cc.

7. The device according to claim 1, characterized in that said insert (6) is made from a semi-rigid absorbent, porous high-density material or a non-absorbent rubber material, comprised between 0.1 g/cc and 0.5 g/cc.

8. The device according to claim 1, characterized in that between the internal lateral wall (2c) of said container (2) and the external lateral surface (3c) of said sponge-like element (3) there is an air gap (7) to permit the latter to undergo a lateral expansion when in use.

9. The device according to claim 8, wherein the air gap (7) is the same from top to bottom.

10. The device according to claim 1, characterized in that said container (2) is shaped like a beaker and has a flanged edge (9) around an opening.

11. The device according to claim 10, characterized in that said container (2), when not in use, is hermetically sealed by an aluminium foil (10) or a plastic material heat-sealed onto said flanged edge (9).

12. The device according to claim 1, characterized in that the container (2) and the sponge-like element (3) are dimensioned in such a way as to be universal and permit any connector present on the market to be housed and disinfected.

13. The device according to claim 1, wherein the sponge-like element (3) is made of polyolefin fibers.

14. The device according to claim 1, wherein the sponge-like element (3) is made of polyolefin fibers and wherein said polyolefin is selected from the group consisting of polyethylene, polypropylene and polyethylene terephthalate.

15. The device according to claim 1, wherein the insert (6) has a longitudinal extent along the axis (1a) of the container (2) that is between one fifth and one half that of the sponge-like element (3).

16. The device according to claim 1, wherein sponges, polyurethanes and foams are not used for the sponge-like element (3).

17. The device according to claim 1, wherein the container (2) is flexible so that an operator can squeeze the container (2) and thereby exert pressure on, and squeeze, the sponge-like element (3).

18. The device accordingly to claim 1, wherein the entire outer lateral surface of the semi-rigid insert (6) engages the adjacent lateral surface of the through cavity (5).

* * * * *